(12) United States Patent
Zheng et al.

(10) Patent No.: US 8,808,697 B2
(45) Date of Patent: Aug. 19, 2014

(54) METHODS OF USE OF SOLUBLE CD24 FOR THERAPY OF RHEUMATOID ARTHRITIS

(75) Inventors: Xincheng Zheng, Ann Arbor, MI (US); Wei Wu, Ypsilanti, MI (US); Yang Liu, Ann Arbor, MI (US); Pan Zheng, Ann Arbor, MI (US)

(73) Assignee: Oncoimmune, Inc., Rockville, MD (US)

( * ) Notice: Subject to any disclaimer, the term of this patent is extended or adjusted under 35 U.S.C. 154(b) by 0 days.

(21) Appl. No.: 13/643,527

(22) PCT Filed: Apr. 28, 2011

(86) PCT No.: PCT/US2011/034282
§ 371 (c)(1),
(2), (4) Date: Feb. 12, 2013

(87) PCT Pub. No.: WO2011/139820
PCT Pub. Date: Nov. 10, 2011

(65) Prior Publication Data
US 2013/0136739 A1     May 30, 2013

Related U.S. Application Data

(60) Provisional application No. 61/329,078, filed on Apr. 28, 2010.

(51) Int. Cl.
*C07K 14/435* (2006.01)
*C07K 14/705* (2006.01)
*C07K 16/46* (2006.01)

(52) U.S. Cl.
USPC ............ 424/134.1; 424/185.1; 424/192.1

(58) Field of Classification Search
None
See application file for complete search history.

(56) References Cited

U.S. PATENT DOCUMENTS

| | | | | |
|---|---|---|---|---|
| 5,726,044 A | * | 3/1998 | Lo et al. | 435/69.7 |
| 6,280,732 B1 | * | 8/2001 | Caras et al. | 424/178.1 |
| 2003/0095966 A1 | * | 5/2003 | Liu et al. | 424/144.1 |
| 2003/0106084 A1 | | 6/2003 | Liu et al. | |
| 2006/0160220 A1 | * | 7/2006 | Bremel et al. | 435/456 |
| 2008/0267980 A1 | | 10/2008 | Tomlinson et al. | |
| 2009/0011407 A1 | | 1/2009 | Liu et al. | |

* cited by examiner

*Primary Examiner* — Phuong Huynh
(74) *Attorney, Agent, or Firm* — Polsinelli PC; Teddy C. Scott, Jr.; Ron Galant

(57) ABSTRACT

Provided herein is a method of treating rheumatoid arthritis using a CD24 protein. The CD24 protein may include mature human or mouse CD24, as well as a N- or C-terminally fused portion of a mammalian immunoglobulin.

6 Claims, 12 Drawing Sheets

FIGURE 1

MGRAMVARLGLGLLLLALLLPTQIYS SETTTGTSSNSSQSTSNSGLAP
NPTNATTK PKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

FIGURE 3

```
Mouse cd24  NQTSVAPFPGN--QNISAS----PNPTNATTRG
            -*   -      *   *    * *        ********--
Human CD24  SETTTGTSS-NSSQSTSNS-GLAPNPTNATTKA(V)
```

The dose dependant therapeutic effect of CD24Fc

SEQUENCE LISTING

<160> NUMBER OF SEQ ID NOS: 6

<210> SEQ ID NO 1
<211> LENGTH: 30
<212> TYPE: PRT
<213> ORGANISM: Homo sapiens

<400> SEQUENCE: 1

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30

<210> SEQ ID NO 2
<211> LENGTH: 31
<212> TYPE: PRT
<213> ORGANISM: Homo sapiens
<220> FEATURE:
<221> NAME/KEY: Xaa
<222> LOCATION: (31)..(31)
<223> OTHER INFORMATION: Val or Ala

<400> SEQUENCE: 2

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Xaa
            20                  25                  30

<210> SEQ ID NO 3
<211> LENGTH: 27
<212> TYPE: PRT
<213> ORGANISM: Mus musculus

<400> SEQUENCE: 3

Asn Gln Thr Ser Val Ala Pro Phe Pro Gly Asn Gln Asn Ile Ser Ala
1               5                   10                  15

Ser Pro Asn Pro Thr Asn Ala Thr Thr Arg Gly
            20                  25

<210> SEQ ID NO 4
<211> LENGTH: 26
<212> TYPE: PRT
<213> ORGANISM: Homo sapiens

<400> SEQUENCE: 4

Met Gly Arg Ala Met Val Ala Arg Leu Gly Leu Gly Leu Leu Leu Leu
1               5                   10                  15

Ala Leu Leu Leu Pro Thr Gln Ile Tyr Ser
            20                  25

<210> SEQ ID NO 5
<211> LENGTH: 287
<212> TYPE: PRT
<213> ORGANISM: Artificial Sequence
<220> FEATURE:
<223> OTHER INFORMATION: Human CD24 IgG1 Fc fusion

<400> SEQUENCE: 5

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro

```
                35                  40                  45
Asn Pro Thr Asn Ala Thr Thr Lys Pro Lys Ser Cys Asp Lys Thr His
 50                  55                  60
Thr Cys Pro Pro Cys Pro Ala Pro Glu Leu Leu Gly Gly Pro Ser Val
 65                  70                  75                  80
Phe Leu Phe Pro Pro Lys Pro Lys Asp Thr Leu Met Ile Ser Arg Thr
                 85                  90                  95
Pro Glu Val Thr Cys Val Val Val Asp Val Ser His Glu Asp Pro Glu
                100                 105                 110
Val Lys Phe Asn Trp Tyr Val Asp Gly Val Glu Val His Asn Ala Lys
            115                 120                 125
Thr Lys Pro Arg Glu Glu Gln Tyr Asn Ser Thr Tyr Arg Val Val Ser
130                 135                 140
Val Leu Thr Val Leu His Gln Asp Trp Leu Asn Gly Lys Glu Tyr Lys
145                 150                 155                 160
Cys Lys Val Ser Asn Lys Ala Leu Pro Ala Pro Ile Glu Lys Thr Ile
                165                 170                 175
Ser Lys Ala Lys Gly Gln Pro Arg Glu Pro Gln Val Tyr Thr Leu Pro
            180                 185                 190
Pro Ser Arg Asp Glu Leu Thr Lys Asn Gln Val Ser Leu Thr Cys Leu
            195                 200                 205
Val Lys Gly Phe Tyr Pro Ser Asp Ile Ala Val Glu Trp Glu Ser Asn
210                 215                 220
Gly Gln Pro Glu Asn Asn Tyr Lys Thr Thr Pro Pro Val Leu Asp Ser
225                 230                 235                 240
Asp Gly Ser Phe Phe Leu Tyr Ser Lys Leu Thr Val Asp Lys Ser Arg
                245                 250                 255
Trp Gln Gln Gly Asn Val Phe Ser Cys Ser Val Met His Glu Ala Leu
            260                 265                 270
His Asn His Tyr Thr Gln Lys Ser Leu Ser Leu Ser Pro Gly Lys
            275                 280                 285

<210> SEQ ID NO 6
<211> LENGTH: 231
<212> TYPE: PRT
<213> ORGANISM: Homo sapiens

<400> SEQUENCE: 6

Pro Lys Ser Cys Asp Lys Thr His Thr Cys Pro Pro Cys Pro Ala Pro
 1               5                  10                  15
Glu Leu Leu Gly Gly Pro Ser Val Phe Leu Phe Pro Pro Lys Pro Lys
                20                  25                  30
Asp Thr Leu Met Ile Ser Arg Thr Pro Glu Val Thr Cys Val Val Val
            35                  40                  45
Asp Val Ser His Glu Asp Pro Glu Val Lys Phe Asn Trp Tyr Val Asp
 50                  55                  60
Gly Val Glu Val His Asn Ala Lys Thr Lys Pro Arg Glu Glu Gln Tyr
 65                  70                  75                  80
Asn Ser Thr Tyr Arg Val Val Ser Val Leu Thr Val Leu His Gln Asp
                 85                  90                  95
Trp Leu Asn Gly Lys Glu Tyr Lys Cys Lys Val Ser Asn Lys Ala Leu
                100                 105                 110
Pro Ala Pro Ile Glu Lys Thr Ile Ser Lys Ala Lys Gly Gln Pro Arg
            115                 120                 125
```

-continued

```
Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

METHODS OF USE OF SOLUBLE CD24 FOR THERAPY OF RHEUMATOID ARTHRITIS

CROSS REFERENCE TO RELATED APPLICATIONS

This claims the benefit of U.S. Provisional Patent Application No. 61/329,078 filed on Apr. 28, 2010, the contents of which are incorporated herein by reference.

FIELD OF THE INVENTION

This invention relates to compositions and methods for treating rheumatoid arthritis.

BACKGROUND OF THE INVENTION

This section provides background information which is not necessarily prior art and a general summary of the present disclosure which is not a comprehensive disclosure of its full scope or all of its features.

CD24 is known as the heat-stable antigen (1). It is expressed as a glycosyl-phosphatidyl-inositol (GPI)-anchored molecule (2) and has a wide distribution in different lineages (3). Because of the tendency of CD24 to be expressed on immature cells, it has also been used as part of stem cell markers and for lymphocyte differentiation. The first function associated with CD24 is a costimulatory activity for antigen-specific T cell response (4-6). In vivo studies indicated that, as a costimulator for T cell activation in the lymphoid organ, CD24 is redundant but becomes essential in the absence of CD28 (7, 8). This would not be the case for local target organs that are not as "costimulator rich". Consistent with this notion, we demonstrated that mice with a targeted mutation of CD24 are completely resistant to induction of experimental autoimmune encephalomyelitis (EAE) (9) (10).

Polymorphisms of human CD24 are associated with risk and progression of several autoimmune diseases (11-15), including multiple sclerosis and rheumatoid arthritis (RA). In cases of multiple sclerosis, we have reported that soluble CD24, consisting of the extracellular portion of murine CD24 and human IgG1 Fc ameliorated the clinical symptom of experimental autoimmune diseases, the mouse model of multiple sclerosis (9). More recent studies by one of us demonstrated that CD24 interact with and represses host response to danger-associated molecular patterns (DAMPs) (16).

RA affects 0.5-1% of human populations. Although a number of disease-modifying antirheumatic drugs (DMARDs) are currently available, even the gold standard of biologic DMARDs, the therapeutics targeting the tumor-necrosis factor alpha, lead to 50% improvement according to American College of Rheumatology Improvement Criteria (ACR50) in less than 50% of the patients receiving the treatments (17). No cure for RA is available. It is therefore necessary to test additional therapeutics for RA. RA is presumed to be autoimmune diseases in the joint, although the cause of the diseases remains largely obscure. A number of studies have implicated T cells in the pathogenesis of rheumatoid arthritis (18). More recently, it has been demonstrated that transfer of antibodies can cause the development of inflammation of the joints of mice (19-21). The pathology of the lesions resembles human rheumatoid arthritis.

One of the most interesting concepts established from the study with passive transfer of RA by antibodies is that tissue-specific autoimmune diseases can be observed even if the antibodies are specific for proteins that are ubiquitously expressed (19-21). This notion is important as it suggest that despite shared pathogenesis, autoimmune diseases to different organs/tissues may require different treatment. In support of this notion, interferon β, which is widely used for treatment of multiple sclerosis, show little effect for treatment of RA (22).

Animal models relevant to human RA played an important role for the advancement of therapeutic development in DMARDs. For example, collagen-induced arthritis in the mouse and rat were critical for the development of therapeutics for RA (23). More recently, it has been demonstrated that adaptive transfer of anti-collagen antibodies cause robust RA-like lesion in the mice (19). Since auto-antibodies are elevated in RA patients prior to the onset of diseases (24, 25), passive transfer of collagen-specific antibody is a relevant model for human RA.

Since the pathogenesis of RA involves host response to DAMP (26, 27) and since the CD24 molecule negatively regulate host response to DAMPs (16), we investigated the potential of using soluble CD24 to treat RA. The passive transfer model of RA was chosen because of both relevance to human diseases and simplicity of experimental designs.

SUMMARY OF THE INVENTION

Provided herein is a method for treating rheumatoid arthritis by administering a CD24 protein to a mammal in need thereof. The CD24 protein may comprise the sequence of mature mouse CD24 or mature human CD24, or a variant thereof. The mature human CD24 may consist of the sequence of SEQ ID NO: 1 or 2. The mature mouse CD24 may consist of the sequence of SEQ ID NO: 3. The CD24 protein may also comprise the extracellular domain of mouse or human CD24, which may be fused to the N-terminal end of the mature CD24. The extracellular domain of CD24 may consist of the sequence of SEQ ID NO: 4. The CD24 protein may further comprise a portion of a mammalian immunoglobulin (Ig), which may be fused to the N-terminus or C-terminus of the mature CD24. The Ig portion may be the Fc portion of a human Ig protein, which may be IgG1, IgG2, IgG3, IgG4, or IgA. The Fc portion may consist of the hinge region and CH2 and CH3 domains of the human Ig protein. The Fc portion may also consist of the hinge region and CH3 and CH4 domains of human IgM.

The CD24 protein may be soluble, and may be glycosylated. The CD24 protein may be produced using a eukaryotic protein expression system. The expression system may comprise a vector contained in a Chinese Hamster Ovary cell line or a replication-defective retroviral vector. The replication-defective retroviral vector may be stably integrated into the genome of a eukaryotic cell.

BRIEF DESCRIPTION OF THE DRAWINGS

FIG. 1. The amino acid composition of the CD24 fusion protein, CD24IgG1Fc (SEQ ID NO: 5). The underlined 26 amino acids are the signal peptide of CD24 (SEQ ID NO: 4). The boxed, bold portion of the sequence is the mature CD24 protein used in the fusion protein (SEQ ID NO: 1). The last amino acid (A or V) that is ordinarily present in the mature CD24 protein has been deleted from the construct to avoid immunogenicity. The non-underlined, non-bold letters are the sequence of IgG1 Fc, including the hinge region and CH1 and CH2 domains (SEQ ID NO: 6).

FIG. 3. Amino acid sequence variations between mature CD24 proteins from mouse (SEQ ID NO: 3) and human (SEQ ID NO: 2). The potential glycosylation sites are bolded, with the N-glycosylation sites in red.

DETAILED DESCRIPTION

Figure 2:
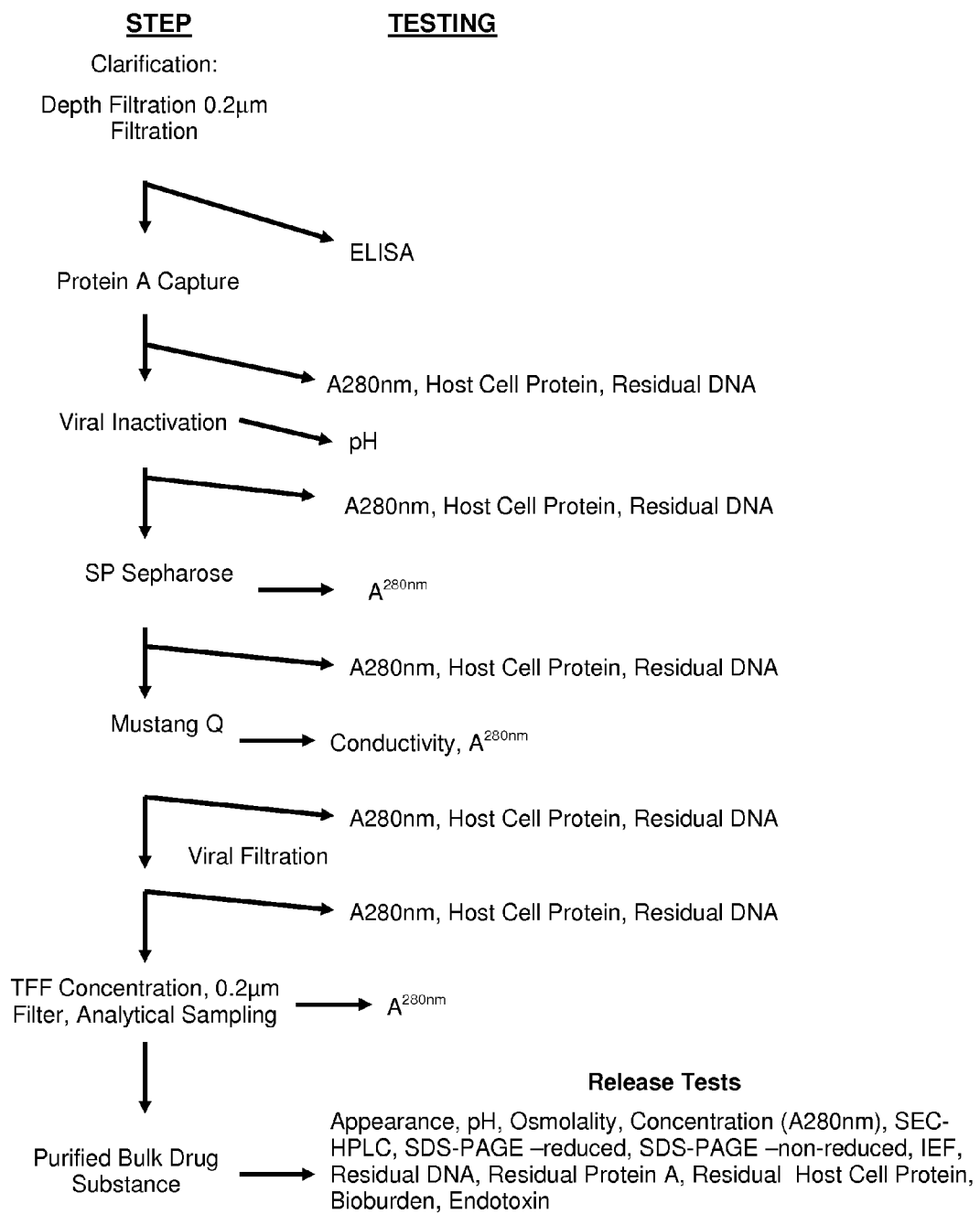
FIG. 2. Methods for purification and processing of CD24IgG1Fc expressed from mammalian cell lines.

The inventors have discovered that a soluble form of CD24 is highly effective for treating rheumatoid arthritis.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6, 9, and 7.0 are explicitly contemplated.

A "peptide" or "polypeptide" is a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

A "variant" may mean means a peptide or polypeptide that differs in amino acid sequence by the insertion, deletion, or conservative substitution of amino acids, but retain at least one biological activity. Representative examples of "biological activity" include the ability to bind to a toll-like receptor and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. CD24

Provided herein is a CD24 protein, which may have the amino acid sequence of mature human CD24, which may be SETTTGTSSNSSQSTSNSGLAPNPTNATTK (SEQ ID NO: 1) or SETTTGTSSNSSQSTSNSGLAPNPTNATTK(V/A) (SEQ ID NO: 2), or mouse CD24, which may be NQTS-VAPFPGNQNISASPNPTNATTRG (SEQ ID NO: 3), or a variant thereof. The CD24 may be soluble. The CD24 may further comprise a N-terminal signal peptide, which may have the amino acid sequence MGRAMVARLGLGLLLLA-LLLPTQIYS (SEQ ID NO: 4). The CD24 may also have an amino acid sequence described in FIG. 1 or 3. The CD24 may exist in one of two allelic forms, such that the C-terminal amino acid of the mature human CD24 may be a valine or an alanine. The C-terminal valine or alanine may be immunogenic and may be omitted from the CD24 to reduce its immunogenicity. The difference between the two alleles may affect the risk of autoimmune diseases, including multiple sclerosis and RA. Nevertheless, since the two allelic forms affect the expression levels of membrane-bounded form, the variation should not affect the function of CD24.

Despite considerable sequence variations in the amino acid sequence of the mature CD24 proteins from mouse and human, they are functionally equivalents in interaction with the danger-associated molecular patterns (DAMP). Since host response to DAMP is considered important for the pathogenesis of RA, the mouse and human CD24 may be functionally equivalent in treating RA. As a result of sequence conservation between mouse and human CD24 primarily in the C-terminus and in the abundance of glycosylation sites, significant variations in the mature CD24 proteins may be tolerated in using the CD24 to treat RA, especially if those variations do not affect the conserved residues in the C-terminus or do not affect the glycosylation sites from either mouse or human CD24.

a. Fusion

The CD24 may be fused at its N- or C-terminal end to a portion of a mammalian Ig protein, which may be human or mouse. The portion may be a Fc region of the Ig protein. The Fc region may comprise the hinge region and CH2 and CH3 domains of the Ig protein. The Ig protein may be human IgG1, IgG2, IgG3, IgG4, IgM, or IgA. The Fc portion may comprise SEQ ID NO: 6. The Ig protein may also be IgM, and the Fc portion may comprise the hinge region and CH3 and CH4 domains of IgM. The CD24 may also be fused at its N- or C-terminus to a protein tag, which may be GST, His, or FLAG. Methods for making fusion proteins and purifying fusion proteins are well known in the art.

b. Production

The CD24 may be heavily glycosylated, and may be involved in functions of CD24 such as costimulation and interaction with danger-associated molecular patterns. The CD24 may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The CD24 may also be produced from a stable cell line that expresses CD24 from a vector or a portion of a vector that has been integrated into the cellular genome. The stable cell line may express CD24 from an integrated replication-defective retroviral vector. The expression system may be GPEx™.

3. Method of Treatment

The CD24 may be used to treat rheumatoid arthritis. The CD24 may be administered to a subject in need thereof. The subject may be a mammal such as a human.

a. Combined CD24 Therapy

The CD24 may be combined with another drug, such as a disease-modifying antirheumatic drug (DMARD). The drug may be a nonsteriod anti-inflammatory drug (NSAID), which may be a propionic acid derivative, an acetic acid derivative, an enolic acid derivative, a fenamic acid derivative, or a selective Cox2 inhibitor. The drug may also be a corticosteroid or Methotrexate. The drug may be a biologic, which may be a TNF-α antagonist such as an anti-TNF-α antibody or a fusion protein that binds to TNF-α (Enbrel), an anti-CD20 mAb, an antagonist of costimulatory molecule CD80 and CD86 such as a monoclonal antibody or a fusion protein (CTLA4Ig) that binds to the two molecules, or an antagonist for a receptor of either IL-1 or IL-6. The CD24 and the other drug may be administrated together or sequentially.

b. Pharmaceutical Composition

The CD24 may be contained in a pharmaceutical composition, which may comprise a solvent, which may keep the CD24 stable over an extended period. The solvent may be PBS, which may keep the CD24 stable for at least 36 months at −20° C. (−15~−25° C.). The solvent may be capable of accommodating the CD24 in combination with the other drug.

c. Dosage

The dose to be used for human may ultimately be determined through a clinical trial to determine a dose with acceptable toxicity and clinical efficacy. The initial clinical dose for human may be estimated through pharmacokinetics and toxicity studies in rodents and non-human primates. The dose of CD24 may be 0.01 mg/kg to 1000 mg/Kg, and may be 1 to 500 mg/kg, depending on the severity of disease being treated and the route of administration.

d. Administration

The route of administration of the pharmaceutical composition may be parenteral. Parenteral administration includes, but is not limited to, intravenous, intraarterial, intraperitoneal, subcutaneous, intramuscular, intrathecal, intraarticular and direct injection into affected joints. For veterinary use, the agent may be administered as a suitably acceptable formulation in accordance with normal veterinary practice. The veterinarian can readily determine the dosing regimen and route of administration that is most appropriate for a particular animal. The pharmaceutical composition may be administered to a human patient, cat, dog, large animal, or an avian.

The CD24 may be administered simultaneously or metronomically with other treatments. The term "simultaneous" or "simultaneously" as used herein, means that the CD24 and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The CD24 may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. The CD24 may be administered at any point prior to a second treatment of the CD24 including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The CD24 may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The CD24 may be administered at any point prior after a previous CD24 treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The following examples are provided to illustrate the methods of the invention and are by no means to limit the use of the methods.

Example 1

Soluble CD24 Proteins

The extracellular domain of CD24 was fused to IgG1 Fc. The amino acid composition of the CD24 fusion protein is provided in FIG. 1. A replication-defective retroviral vector that drives expression of the CD24Ig fusion protein was then generated. The GPEx™ (an acronym for gene product expression) system offers several important advantages, the most important of which is the, on average, >1000 insertions/cell but with only 1 copy/insertion. Moreover, since the retrovirus preferentially inserts into the transcriptional active locus, the GPEx™ resulted in a high level of expression of the targeted protein. Stable cell lines that produce a high yield of CD24Ig were generated. In addition 45 grams of GLP grade products and ~100 grams of cGMP grade products were produced. The methods used for downstream processing of media harvested from the bioreactor are summarized in the flow chart below (FIG. 2).

Harvest Clarification

The bioreactor culture media was clarified using Cuno 60M02 Maximizer depth filters followed by a Millipore Opticap 0.22 um filter. The filtrate was collected into a sterile collection bag. Samples were obtained for CD24-Fc yield quantitation by ELISA.

Protein A Capture

The clarified media was passed over a column of Protein A resin (GE Healthcare MabSelect) at a concentration not exceeding 16 g/L of resin (based on ELISA) and a contact time of 4 minutes. The column was washed with the equilibration buffer (50 mM Tris+0.15M NaCl pH7.5), then with 10 mM sodium citrate/citric acid pH 6.0 for 5cvs. Bound CD24Ig was eluted from the column using 10 mM sodium citrate/citric acid pH 3.5

Viral Inactivation

The Protein A eluate fraction was immediately brought to pH 3.0 with the addition of 2M Hydrochloric acid and held at this pH for 30 minutes at ambient temperature. It was then brought to pH 5.0 with the addition of 1M Tris base, and filtered to clarity using a 0.65 um glass fiber filter (Sartorius Sartopure GF2) and 0.2 um (Sartorius Sartopore 2) into a sterile collection bag.

SP-Sepharose Chromatography

The viral inactivated material was applied to a column of SP-Sepharose (GE Healthcare) at a concentration not exceeding 25 g/L of resin (based on A280 nm of 1.22=1 mg/mL) and a linear flow rate of 250 cm/hr. The column was washed with the equilibration buffer (10 mM sodium citrate/citric acid pH 5.0) and bound CD24Ig was eluted from the column using 10 mM sodium citrate/citric acid+0.2M NaCl pH5.0. The effluent was collected into a sterile collection bag.

Mustang Q Chromatography

The SP-Sepharose elute was adjusted to pH 7.5 by the addition of 1M Tris base and diluted with WFI to reduce the conductivity. The diluted material was applied to a Mustang Q filter (Pall) at a concentration not exceeding 0.5 g/L of resin (based on A280 nm of 1.22=1 mg/mL) and at a flow rate of 5 column volumes/minute. The filter was washed with the equilibration buffer (10 mM Tris pH 7.5) and the CD24-Fc is contained in the flow through and is collected into a sterile collection bag.

Viral Filtration

The Mustang Q flow through was then filtered at a constant pressure of 30 psi through a 0.2 mM filter and a Millipore NFP viral filter (nominal pore size 20 nm) and was collected into a sterile collection bag.

Concentration and Final Formulation

The product was concentrated and diafiltered using a 10 kDa ultrafiltration membrane (Millipore Prep/Scale) into a 10 mM sodium phosphate, 150 mM sodium chloride pH 7.2 at approximately 10 mg/mL final concentration as determined by absorbance at 280 nm. Analytical samples were drawn from the bulk whilst in a biosafety cabinet. Labeling was performed and the samples were delivered to QC for testing while the bulk aliquots were stored at 2-8° C. pending release.

Viral Clearance Studies

The viral clearance validation was performed at Cardinal Health, NC, on samples prepared at CHM. Qualified scientists from Gala Biotech performed the chromatography and filtration steps in the Cardinal Health Viral Validation facility with the assistance of Cardinal Health personnel. The scale down procedure was developed from the 200 L scale process. Two viruses were chosen to be used in this study. The first was Xenotropic murine Leukemia virus (XMuLv), which is an enveloped RNA virus of 80-130 nm in size from the Retroviridae viral family. The second was Porcine Parvovirus (PPV), which is a nonenveloped DNA virus of 18-26 nm in size. This is considered a robust virus, and was expected to demonstrate a much lower viral reduction through the purification protocol than the XMuLv.

Example 2

Use of CD24Fc for Therapy of RA

Figure 4:
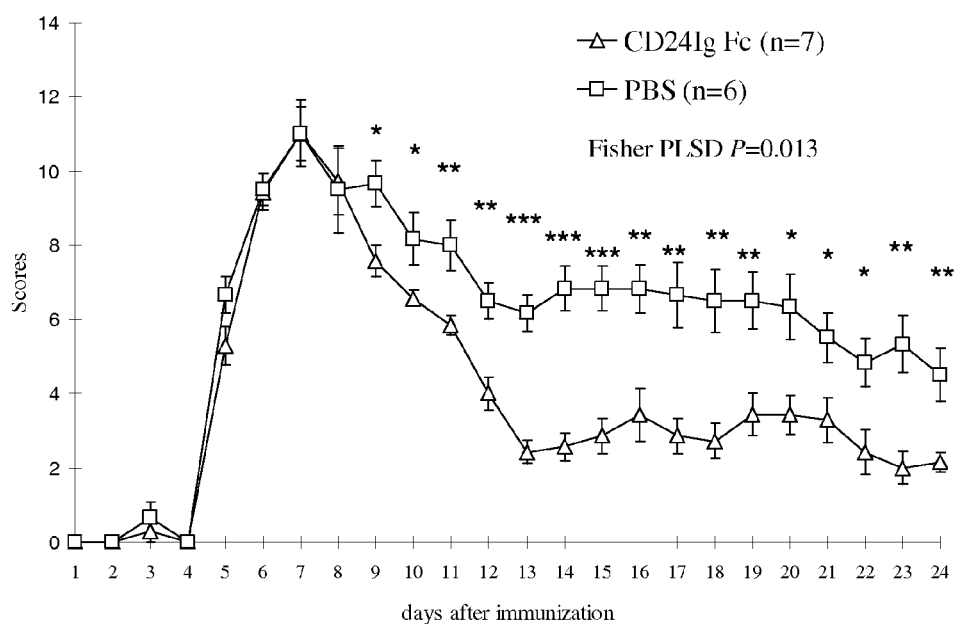
FIG. 4. Therapeutic effect of CD24Ig for RA. 8-10 weeks male BALB/c mice were immunized intravenously with 2 mg/mouse ArthritoMab arthritis inducing antibody cocktail (MDbioproducts, St Paul, Minn.). 2 days later, the mice were i.p. injected with 90 μg LPS dissolved in PBS. The disease progress was monitored daily with the following score system. 0. No reaction, normal; 1, Mild, but definite redness and swelling of the ankle/wrist or apparent redness and swelling limited to individual digits, regardless of the number of affected digits; 2, Moderate to severe redness and swelling of the ankle/wrist; 3, Redness and swelling of the entire paw; 4, Maximally inflamed limb including digits, with involvement of multiple joints. The data shown are composite scores from four limbs (mean±SE). * $P<0.05$,  $P<0.01$, * $P<0.001$. The difference between the two groups is also significant based on Fisher PLSD test.

This example demonstrates that CD24 can be used to treat RA. Because anti-collagen antibodies are present in RA patients before the disease onset, and because the anti-collagen antibodies are capable of inducing RA-like pathology in the mice, the established passive transfer model of RA was used to test the efficacy of soluble CD24. The fusion protein was dissolved in PBS vehicle at 10 mg/ml. As shown in FIG. 4, a combination of 4 anti-collagen antibodies caused severe clinical symptoms in all limbs, which peaked at day 7 in both vehicle and CD24Fc treated groups. The diseases were characterized by redness and swelling of the entire paw in all limbs. Some limbs are maximally inflamed that involve digits and multiple joints. Therefore, the soluble protein does not affect the initiation of the diseases. Surprisingly, the CD24Fc treated group show much more rapid recovery. The reductions in clinical scores are highly significant starting on day 9 and last throughout the entire observation period of 24 days. Thus, CD24Fc provides an effective treatment for RA. Interestingly, since the effect is observed after the peak of disease, it is likely that blocking CD24 affect the chronic disease process after initiation of the inflammation.

Example 3

Figure 5:
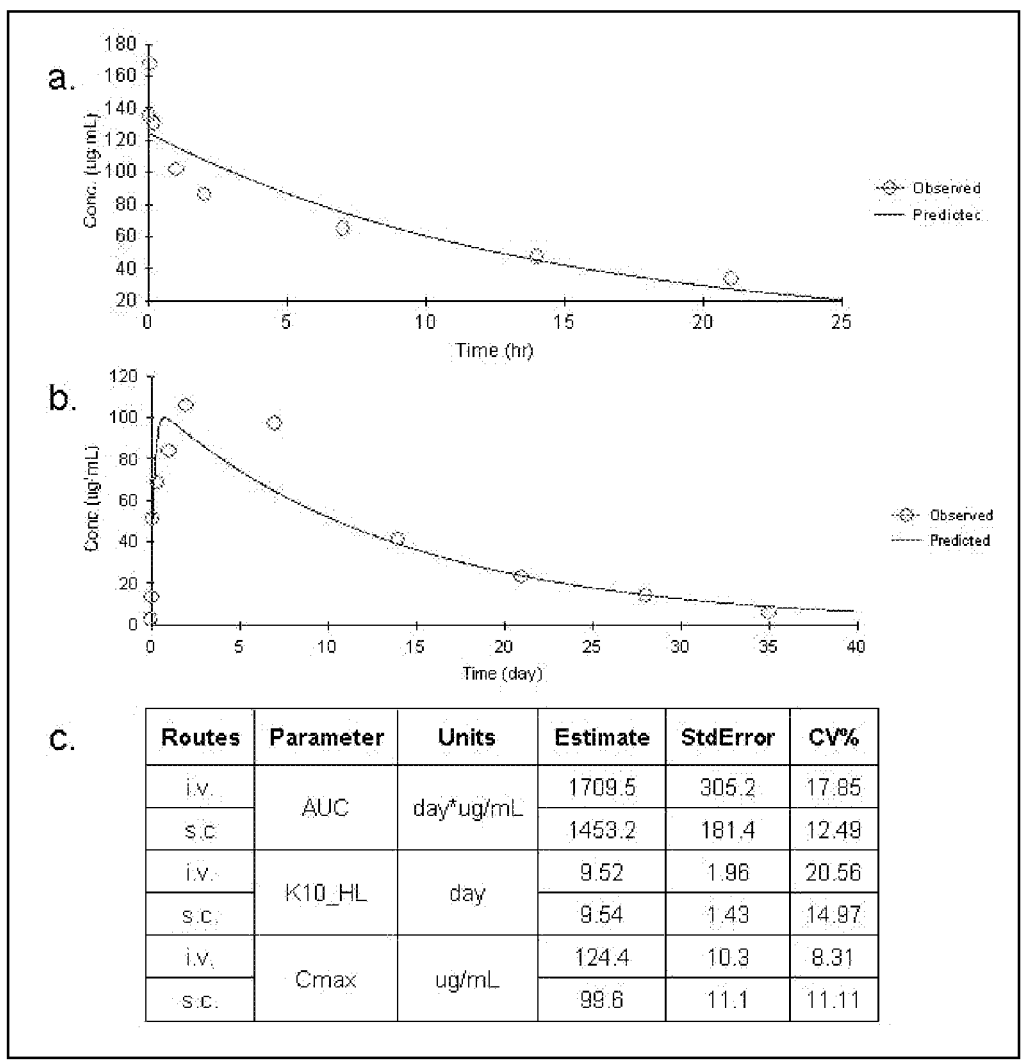
FIG. 5. WinNonlin compartmental modeling analysis of pharmacokenitics of CD24IgG1. The opened circles represent the average of 3 mice, and the line is the predicted pharmacokinetic curve. a. i.v. injection of 1 mg CD24IgG1. b. s.c. injection of 1 mg CD24IgG1. c. Comparison of the total amounts of antibody in the blood as measured by areas under curve (AUC), half-life and maximal blood concentration. Note that overall, the AUC and $C_{max}$ of the s.c. injection is about 80% of i.v. injection, although the difference is not statistically significant.

CD24 Pharmacokinetics 1 mg of CD24IgG1 was injected into naïve C57BL/6 mice and collected blood samples at different timepoints (5 min, 1 hr, 4 hrs, 24 hrs, 48 hrs, 7 days, 14 days and 21 days) with 3 mice in each timepoint. The sera were diluted 1:100 and the levels of CD24Ig was detected using a sandwich ELISA using purified anti-human CD24 (3.3 µg/ml) as the capturing antibody and peroxidase conjugated goat anti-human IgG Fc (5 µg/ml) as the detecting antibodies. As shown in FIG. 5a. The decay curve of CD24Ig revealed a typical biphase decay of the protein. The first biodistribution phase had a half life of 12.4 hours. The second phase follows a model of first-order elimination from the central compartment. The half life for the second phase was 9.54 days, which is similar to that of antibodies in vivo. These data suggest that the fusion protein is very stable in the blood stream. In another study in which the fusion protein was injected subcutaneously, an almost identical half life of 9.52 days was observed (FIG. 5b). More importantly, while it took approximately 48 hours for the CD24Ig to reach peak levels in the blood, the total amount of the fusion protein in the blood, as measured by AUC, was substantially the same by either route of injection. Thus, from therapeutic point of view, different route of injection should not affect the therapeutic effect of the drug. This observation greatly simplified the experimental design for primate toxicity and clinical trials.

Example 4

CD24 for Treating RA

For decades, it has been assumed that RA is predominantly a T-cell mediated autoimmune diseases. In the last two decades, there is a reawaking on the possible role for antibodies and B lymphocytes in RA pathogenesis. Thus, in addition or rheumatoid factors, a host of autoreactive antibodies have been found in RA patients, although it has not been definitively addressed in human. However, several lines of evidence have demonstrated that in the mouse models, antibodies specific for either ubiquitous or tissue specific antigens are sufficient to cause RA symptoms. For instance, antibodies from the K/BxN TCR transgenic mice were found to be fully capable of transferring RA-like diseases in the new host. Likewise, a cocktail for 4 anti-collagen antibodies is now widely used to induce RA in the mouse. This model is now called CAIA, for collagen antibody-induced arthritis.

Genetic analyses of CAIA model indicate critical roles for complement. Although other possibilities exist, these requirements suggest potential involvement of antibody-mediated tissue damage in the pathogenesis of RA. The linkage between tissue damage and inflammation is a long-standing observation in immunology. Nearly two decades ago, Matzinger proposed what was popularly called danger theory. In essence, she argued that the immune system is turned on when it senses the dangers in the host. Although the nature of danger was not well defined at the time, it has been determined that necrosis is associated with the release of intracellular components such as HMGB1 and Heat-shock proteins, which were called DAMP, for danger-associated molecular patterns. DAMP were found to promote production of inflammatory cytokines and autoimmune diseases. In animal models, inhibitors of HMGB1 and HSP90 were found to ameliorate RA. The involvement of DAMP raised the prospect that negative regulation for host response to DAMP can be explored for RA therapy.

CD24-Siglec 10 Interaction in Host Response to Tissue Injuries

Figure 6:
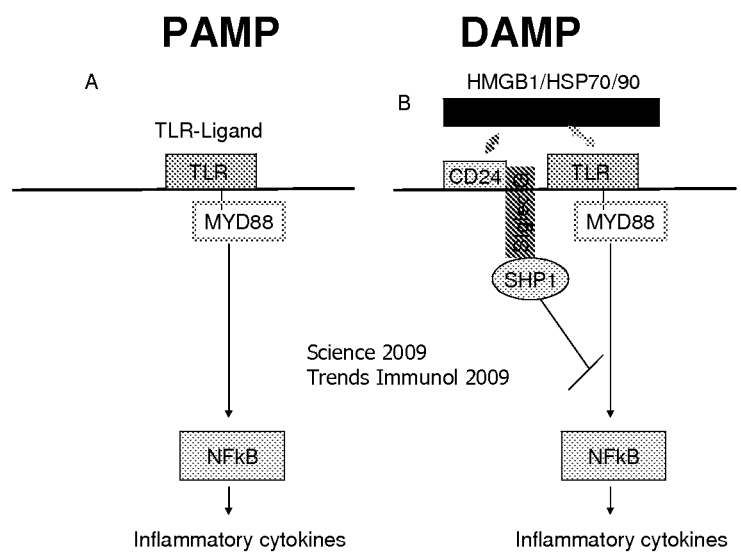
FIG. 6. CD24-Siglec G (10) interaction discriminates between PAMP and DAMP. A. Host response to PAMP was unaffected by CD24-Siglec G(10) interaction. B. CD24-Siglec G (10) interaction represses host response to DAMP, possibly through the Siglec G/10-associated SHP-1.

Using acetaminophen-induced liver necrosis and ensuring inflammation, we observed that through interaction Siglec G, CD24 provides a powerful negative regulation for host response to tissue injuries. CD24 is a GPI anchored molecules that is broadly expressed in hematopoietic cells and other tissue stem cells. Genetic analysis of a variety of autoimmune disease in human, including multiple sclerosis, systemic lupus erythromatosus, RA, and giant cell arthritis, showed significant association between CD24 polymorphism and risk of autoimmune diseases. Siglec G is a member of I-lectin family, defined by their ability to recognize sialic acid containing structure. Siglec G recognized sialic acid containing structure on CD24 and negatively regulates production of inflammatory cytokines by dendritic cells (16). In terms of its ability to interact with CD24, human Siglec 10 and mouse Siglec G are functionally equivalent. However, it is unclear if there is a one-to-one correlation between mouse and human homologues. Although the mechanism remains to be full elucidated, it is plausible that SiglecG-associated SHP1 may be involved in the negative regulation. These data, reported in Science recently, leads to a new model in which CD24-Siglec G/10 interaction may play a critical in discrimination pathogen-associated molecular pattern (PAMP) from DAMP (FIG. 6).

At least two overlapping mechanisms may explain the function of CD24. First, by binding to a variety of DAMP, CD24 may trap the inflammatory stimuli to prevent their interaction with TLR or RAGE. This notion is supported by observations that CD24 is associated with several DAMP molecules, including HSP70, 90, HMGB1 and nucleolin. Second, perhaps after associated with DAMP, CD24 may stimulate signaling by Siglec G. Both mechanisms may act in concert as mice with targeted mutation of either gene mounted much stronger inflammatory response. In fact, DC cultured from bone marrow from either CD24-/- or Siglec G-/- mice produced much higher inflammatory cytokines when stimulated with either HMGB1, HSP70, or HSP90. In contrast, no effect were found in their response to PAMP, such as LPS and PolyI:C. These data not only provided a mechanism for the innate immune system to distinguish pathogen from tissue injury, but also suggest that CD24 and Siglec G as potential therapeutic targets for diseases associated with tissue injuries.

Therapeutic Effect of CD24Fc on Collagen-antibody-induced Arthritis

Given the suspected role for innate immunity to tissue injury in the pathogenesis of RA and the role for CD24-Siglec G/10 pathway in negatively regulate such response, the possibility of stimulating this pathway to treat RA was explored. Pathogenesis of essentially all autoimmune diseases involves induction of immune response to autoantigen and autoimmune destruction. The autoimmune destructive phase was focused on, based the novel function of CD24-Siglec G interaction. Therefore, for the preliminary analysis, collagen antibody-induced arthritis model was adopted to evaluate potential therapeutic effect.

Figure 7:
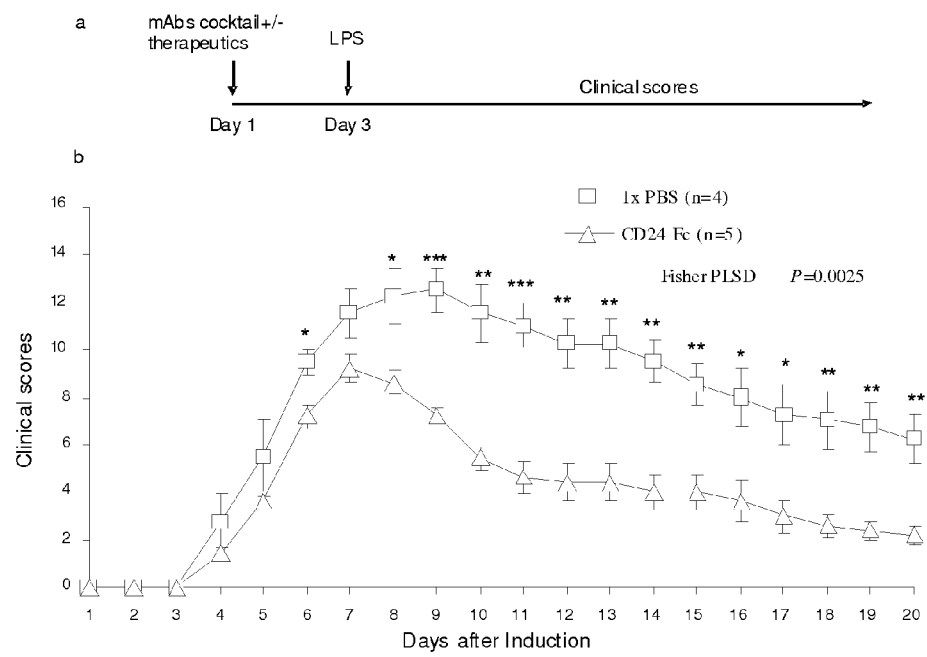
FIG. 7. A single injection of CD24Fc reduces clinical score of CAIA. a. Diagram of experiments. BALB/c mice (8 weeks old) received mAbs on day 1 in conjunction with either vehicle or fusion proteins. The mice were injected LPS on day 3, and were observed daily for 3 weeks. b. CD24Fc reduces clinical scores of CAIA. The fusion proteins (1 mg/mouse) or vehicles were injected once on day 1. Clinical scores were determined double blind. *, $P<0.05$; , $P<0.01$; *, $P<0.001$. The effect of CD24 was reproduced in 6 independent experiments, involving a total of 52 mice in the PBS group and 54 mice in CD24Fc group.

As shown in FIG. 7a, the CAIA was induced on 8 weeks old BALB/c mice by i.v. injection of a cocktail of 4 anti-collagen mAbs (MD Biosciences, St. Paul, Minn.) at 2 mg/mouse on day 1, and i.p. injection of 100 µg/mouse of LPS (MD Bioscience) on day 3. The mice were treated on day 1 with either 1 mg CD24Fc or equal volume of 1×PBS vehicle as negative control. As shown in FIG. 7b, in comparison with vehicle control, CD24Fc provided highly significant therapeutic effects.

Figure 8:
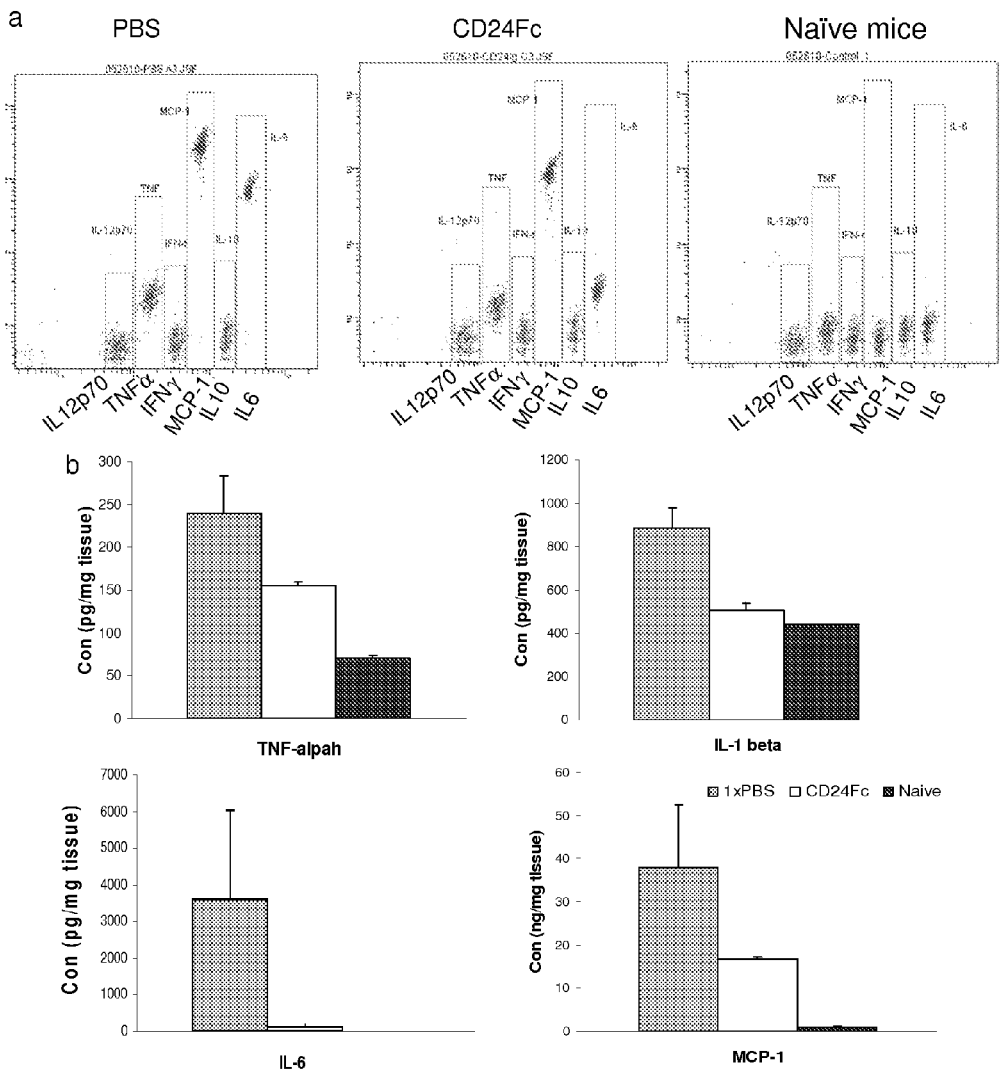
FIG. 8. CD24Fc reduces the levels of inflammatory cytokines in the joint and CAIA. CAIA initiated and treated as diagramed in FIG. 7a. The inflammatory cytokines were measured by cytokine bead array from BD pharmingen. a. Representative FACS profile. b. The summary of reduced cytokines (Mean±SE) measured in the joint homogenates.

To understand the mechanism by which CD24Fc reduces arthritis in this model, cytokines were measured from homogenized joints of CD24Fc treated mice or PBS control group, and measured the supernatant of 200 µg tissue homogenates by cytokine beads array. A typical example is shown in FIG. 8a, while the summary data are shown in FIG. 8b. These data demonstrated that systematically administrated CD24 reduces the levels of multiple inflammatory cytokines including TNF-α, IL-6, MCP-1(CCL2) and IL-1β.

Figure 9:
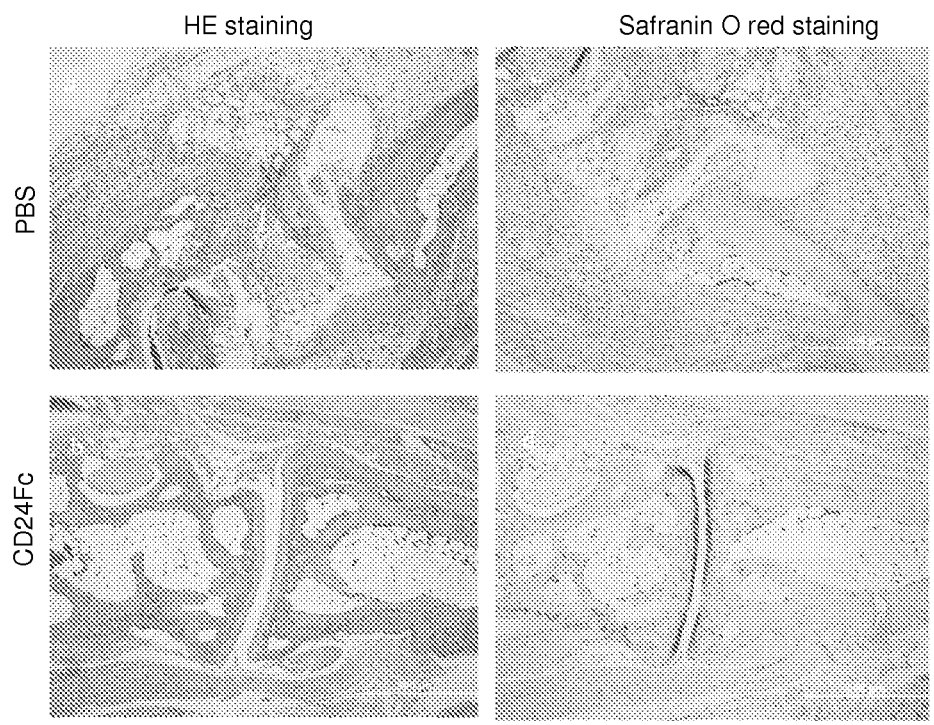
FIG. 9. CD24Fc reduces inflammation and destruction of cartilage in the joint. On day 7, front and hind paws were dissected from both CD24Fc treated and control mice, fixed in 4% paraformaldehyde for 24 hours followed by decalcification with 5% formic acid. The paws were then embedded in paraffin and the longitudinal section were stained with H&E and Safranin 0 red (Sigma-Aldrich).

The effect of CD24Fc is substantiated by histological analysis of the synovial joints of CAIA mice, as presented in FIG. 9. On day 7 after induction of arthritis, H&E staining demonstrated that the joint synoviums in the PBS group are heavily infiltrated with inflammatory cells including neutrophil, macrophage, and lymphocytes (FIG. 9a). This was much reduced in the CD24Fc treated mice (FIG. 9b). In addition, sever cartilage damages were revealed by the loss of safranin O red staining in PBS-treated (FIG. 9c) mice, but not CD24Fc-treated group (FIG. 9d).

Figure 10:
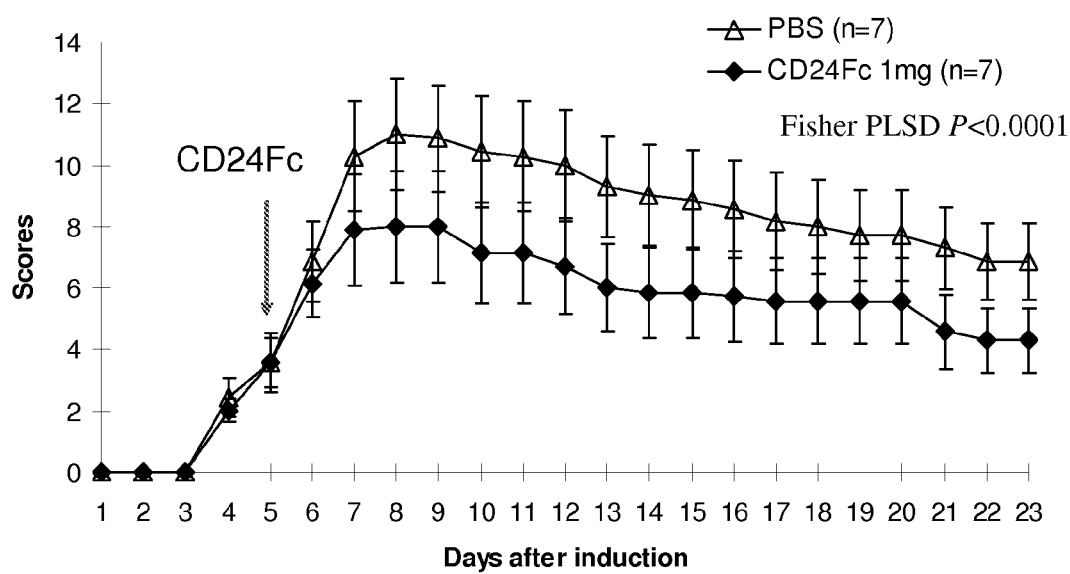
FIG. 10. Therapeutic effect of CD24Fc administrated on day 5 of CAIA induction. The CAIA-induced mice were randomized into two groups, receiving either vehicle (PBS) or CD24 Fc. The mice were scored double blind. Representative of three independent experiments are shown.

To determine whether mice, CD24Fc have therapeutic effect on ongoing RA, treatment was started at either 5 or 7 days after induction of RA. As shown in FIG. 10, significant reduction of RA score was observed as soon as two days after CD24Fc treatment. The therapeutic effect lasted for the remaining period of observation even without additional treatment. These data further strengthen the therapeutic potential of CD24Fc on ongoing diseases.

Figure 11:
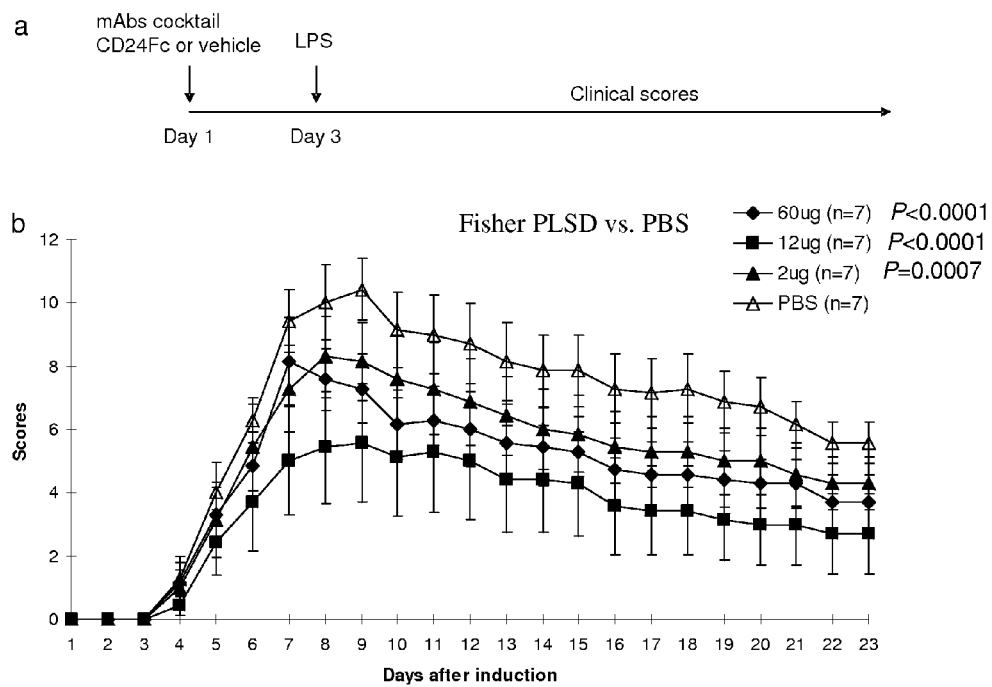
FIG. 11. Low doses of CD24Fc prevent development of CAIA. a. Diagram of experiments. b. Clinical scores of arthritis, scored double blind.

In order to estimate the therapeutic doses of CD24Fc in human, CD24Fc was titrated through a wide range of doses. As shown in FIG. 11, as little as 2 microgram/mice is sufficient to have statistically significant therapeutic effect.

Siglecg-dependent Therapeutic Effect of CD24Fc

Figure 12:
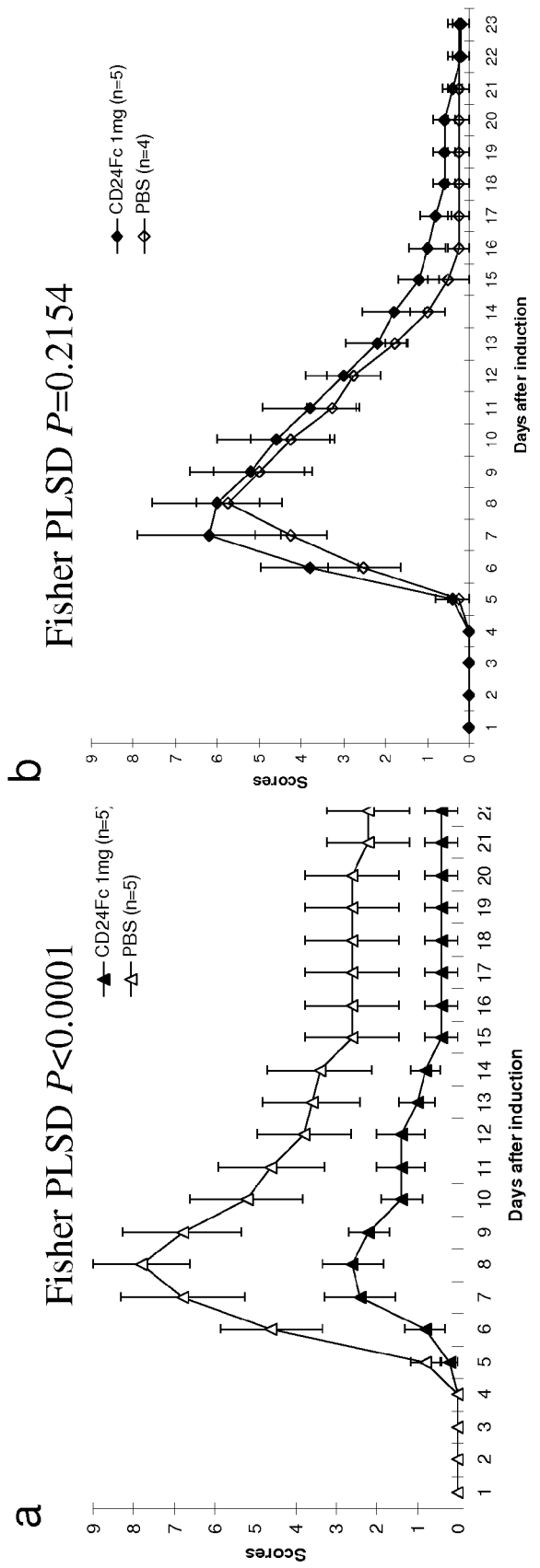
FIG. 12. Siglecg is essential for therapeutic effect of CD24Fc, WT (a) and Siglecg−/− mice (b) were received either vehicle control or CD24Fc in conjunction of a cocktail of anti-collagen mAbs. The clinical scores were recorded daily double blind.

To determine whether CD24Fc protect mice by interacting with Siglec G, we determined if the therapeutic effect depends on the Siglecg gene. Since the Siglecg-deficient mice were produced with ES cells from C57BL/6 mice, we used WT C57BL/6 mice as control. As shown in FIG. 12a, since the B6 mice are known to be less susceptible to the CAIA, the overall disease score is lower than that observed in the BALB/c mice. Nevertheless, a single injection of the CD24Fc essentially wiped out the clinical signs in the WT mice. Importantly, even though the disease is less severe in the Siglecg-deficient mice, CD24Fc had no therapeutic effect. Therefore, the therapeutic effect of CD24Fc is strictly dependent on the Siglecg gene.

Taken together, the data described herein demonstrates high therapeutic efficacy of CD24Fc for CAIA. Given our extensive data on safety, stability and our successful manufacture of CD24Fc all point to great potential of the fusion protein as a therapeutic for RA.

Example 5

Toxicity

Extensive toxicity studies of rodent and non-human primates have shown no drug-related toxicity at doses from 12.5 to 125 mg/kg in mouse and non-human primates.

REFERENCES CITED

1. Springer, T., G. Galfre, D. S. Secher, and C. Milstein. 1978. Monoclonal xenogeneic antibodies to murine cell surface antigens: identification of novel leukocyte differentiation antigens. Eur J Immunol 8:539-551.

2. Pierres, M., P. Naquet, J. Barbet, S. Marchetto, I. Marics, C. Devaux, M. Barad, R. Hyman, and G. Rougon. 1987. Evidence that murine hematopoietic cell subset marker J11d is attached to a glycosyl-phosphatidylinositol membrane anchor. Eur J Immunol 17:1781-1785.

3. Rougon, G., L. A. Alternan, K. Dennis, X. J. Guo, and C. Kinnon. 1991. The murine heat-stable antigen: a differentiation antigen expressed in both the hematolymphoid and neural cell lineages. Eur J Immunol 21:1397-1402.

4. Liu, Y., and C. A. J. Janeway. 1992. Cells that present both specific ligand and the costimulatory activity are the most efficient inducer of clonal expansion of normal CD4 T cells. Proc Natl Acad Sci USA 89:3845-3849.

5. Liu, Y., B. Jones, A. Aruffo, K. M. Sullivan, P. S. Linsley, and C. A. Janeway, Jr. 1992. Heat-stable antigen is a costimulatory molecule for CD4 T cell growth. J Exp Med 175:437-445.

6. Liu, Y., B. Jones, W. Brady, C. A. Janeway, Jr., P. S. Linsley, and P. S. Linley. 1992. Co-stimulation of murine CD4 T cell growth: cooperation between B7 and heat-stable antigen [published erratum appears in Eur J Immunol 1993 March; 23(3):780]. Eur J Immunol 22:2855-2859.

7. Liu, Y., R. H. Wenger, M. Zhao, and P. J. Nielsen. 1997. Distinct costimulatory molecules are required for the induction of effector and memory cytotoxic T lymphocytes. J Exp Med 185:251-262.

8. Wu, Y., Q. Zhou, P. Zheng, and Y. Liu. 1998. CD28-independent induction of T helper cells and immunoglobulin class switches requires costimulation by the heat-stable antigen. J Exp Med 187:1151-1156.

9. Bai, X. F., J. Q. Liu, X. Liu, Y. Guo, K. Cox, J. Wen, P. Zheng, and Y. Liu. 2000. The heat-stable antigen determines pathogenicity of self-reactive T cells in experimental autoimmune encephalomyelitis. J Clin Invest 105:1227-1232.

10. Bai, X. F., O. Li, Q. Zhou, H. Zhang, P. S. Joshi, X. Zheng, Y. Liu, Y. Wang, and P. Zheng. 2004. CD24 Controls Expansion and Persistence of Autoreactive T Cells in the Central Nervous System during Experimental Autoimmune Encephalomyelitis. J Exp Med 200:447-458.

11. Otaegui, D., A. Saenz, P. Camano, L. Blazquez, M. Goicoechea, J. Ruiz-Martinez, J. Olaskoaga, J. A. Emparanza, and A. Lopez de Munain. 2006. CD24 V/V is an allele associated with the risk of developing multiple sclerosis in the Spanish population. Mult Scler 12:511-514.

12. Rueda, B., J. A. Miranda-Filloy, J. Martin, and M. A. Gonzalez-Gay. 2008. Association of CD24 gene polymorphisms with susceptibility to biopsy-proven giant cell arteritis. J. Rheumatol. 35:850-854.

13. Sanchez, E., A. K. Abelson, J. M. Sabio, M. A. Gonzalez-Gay, N. Ortego-Centeno, J. Jimenez-Alonso, E. de Ramon, J. Sanchez-Roman, M. A. Lopez-Nevot, I. Gunnarsson, E. Svenungsson, G. Sturfelt, L. Truedsson, A. Jonsen, M. F. Gonzalez-Escribano, T. Witte, M. E. Alarcon-Riquelme, and J. Martin. 2007. Association of a CD24 gene polymorphism with susceptibility to systemic lupus erythematosus. Arthritis Rheum. 56:3080-3086.

14. Wang, L., S. Lin, K. Rammohan, Z. Liu, J. Liu, R.-H. Liu, N. Guinther, Q. Zhou, T. Wang, X. Zheng, D. J. Birmingham, B. H. Rovin, L. A. Herbert, Y. Wu, D. J. Lynn, G. Cooke, C. Y. Yu, P. Zheng, and Y. Liu. 2007. A di-nucleotide deletion in CD24 confers protection against autoimmune diseases. Plos Genetics 3:e49.

15. Zhou, Q., K. Rammohan, S. Lin, N. Robinson, O. Li, X. Liu, X. F. Bai, L. Yin, B. Scarberry, P. Du, M. You, K. Guan, P. Zheng, and Y. Liu. 2003. CD24 is a genetic modifier for risk and progression of multiple sclerosis. Proceedings of the National Academy of Sciences of the United States of America 100:15041-15046.

16. Chen, G. Y., J. Tang, P. Zheng, and Y. Liu. 2009. CD24 and Siglec-10 Selectively Repress Tissue Damage-Induced Immune Responses. Science 323:1722-1725.

17. Wiens, A., R. Venson, C. J. Correr, M. F. Otuki, and R. Pontarolo. Meta-analysis of the efficacy and safety of adalimumab, etanercept, and infliximab for the treatment of rheumatoid arthritis. Pharmacotherapy 30:339-353.

18. Panayi, G. S., J. S. Lanchbury, and G. H. Kingsley. 1992. The importance of the T cell in initiating and maintaining the chronic synovitis of rheumatoid arthritis. Arthritis Rheum 35:729-735.

19. Banda, N. K., J. M. Thurman, D. Kraus, A. Wood, M. C. Carroll, W. P. Arend, and V. M. Holers. 2006. Alternative complement pathway activation is essential for inflammation and joint destruction in the passive transfer model of collagen-induced arthritis. J Immunol 177:1904-1912.

20. Korganow, A. S., H. Ji, S. Mangialaio, V. Duchatelle, R. Pelanda, T. Martin, C. Degott, H. Kikutani, K. Rajewsky, J. L. Pasquali, C. Benoist, and D. Mathis. 1999. From systemic T cell self-reactivity to organ-specific autoimmune disease via immunoglobulins. Immunity 10:451-461.

21. Maccioni, M., G. Zeder-Lutz, H. Huang, C. Ebel, P. Gerber, J. Hergueux, P. Marchal, V. Duchatelle, C. Degott, M. van Regenmortel, C. Benoist, and D. Mathis. 2002. Arthritogenic monoclonal antibodies from K/BxN mice. J Exp Med 195:1071-1077.

22. van Holten, J., K. Pavelka, J. Vencovsky, H. Stahl, B. Rozman, M. Genovese, A. J. Kivitz, J. Alvaro, G. Nuki, D. E. Furst, G. Herrero-Beaumont, I. B. McInnes, P. Musikic, and P. P. Tak. 2005. A multicentre, randomised, double blind, placebo controlled phase II study of subcutaneous interferon beta-1a in the treatment of patients with active rheumatoid arthritis. Ann Rheum Dis 64:64-69.

23. Vilcek, J., and M. Feldmann. 2004. Historical review: Cytokines as therapeutics and targets of therapeutics. Trends in pharmacological sciences 25:201-209.

24. Rantapaa-Dahlqvist, S., B. A. de Jong, E. Berglin, G. Hallmans, G. Wadell, H. Stenlund, U. Sundin, and W. J. van Venrooij. 2003. Antibodies against cyclic citrullinated peptide and IgA rheumatoid factor predict the development of rheumatoid arthritis. Arthritis Rheum 48:2741-2749.

25. van Venrooij, W. J., and G. J. Pruijn. 2000. Citrullination: a small change for a protein with great consequences for rheumatoid arthritis. Arthritis research 2:249-251.

26. Jiang, W., and D. S. Pisetsky. 2007. Mechanisms of Disease: the role of high-mobility group protein 1 in the pathogenesis of inflammatory arthritis. Nature clinical practice 3:52-58.

27. van Beijnum, J. R., W. A. Buurman, and A. W. Griffioen. 2008. Convergence and amplification of toll-like receptor (TLR) and receptor for advanced glycation end products (RAGE) signaling pathways via high mobility group B1 (HMGB1). Angiogenesis 11:91-99.

28. Sanchez, E., B. Fernandez-Gutierrez, M. A. Gonzalez-Gay, A. Balsa, A. Garcia, L. Rodriguez, D. Pascual-Salcedo, M. F. Gonzalez-Escribano, and J. Martin. 2008. Investigating the role of CD24 gene polymorphisms in rheumatoid arthritis. Ann Rheum Dis 67:1197-1198.

29. Kay, R., P. M. Rosten, and R. K. Humphries. 1991. CD24, a signal transducer modulating B cell activation responses, is a very short peptide with a glycosyl phosphatidylinositol membrane anchor. J Immunol 147:1412-1416.

30. Kay, R., F. Takei, and R. K. Humphries. 1990. Expression cloning of a cDNA encoding M1/69-j11d heat-stable antigens. J Immunol 145:1952-1959.

31. Motari, E., X. Zheng, X. Su, Y. Liu, M. Kvaratskhelia, M. Freitas, and P. G. Wang. 2009. Analysis of Recombinant CD24 Glycans by MALDI-TOF-MS Reveals Prevalence of Sialyl-T Antigen. American journal of biomedical sciences 1:1-11.

32. Liu, Y. 1994. The costimulatory pathway for T cell response. RG Landes (ed.), Austin, TX: CRC Press, pp. 1-122.

The invention claimed is:

1. A CD24 protein comprising SEQ ID NO: 5.
2. The CD24 protein of claim 1, wherein the CD24 protein is soluble.
3. The CD24 protein of claim 1, wherein the CD24 protein is glycosylated.
4. The CD24 protein of claim 1, wherein the CD24 protein is produced using a eukaryotic protein expression system.
5. The CD24 protein of claim 4, wherein the expression system comprises a vector contained in a Chinese Hamster Ovary cell line or a replication-defective retroviral vector.
6. The CD24 protein of claim 5, wherein the replication-defective retroviral vector is stably integrated into the genome of a eukaryotic cell.

* * * * *